United States Patent
Bokser et al.

(10) Patent No.: US 11,931,271 B2
(45) Date of Patent: Mar. 19, 2024

(54) PROSTHETIC FOOT WITH SWITCHABLE WALKING AND JOGGING MODES

(71) Applicant: Liberating Technologies, Inc., Holliston, MA (US)

(72) Inventors: Benjamin Bokser, Flushing, NY (US); Kevin Keough, Sharon, MA (US); Aaron Taszreak, China, MI (US); Todd Farrell, Waltham, MA (US); Jennifer Johansson, Wayland, MA (US); Sangwoo Park, Moriches, NY (US); Kevin Lawrence, Milford, MA (US)

(73) Assignee: Liberating Technologies, Inc., Holliston, MA (US)

( * ) Notice: Subject to any disclaimer, the term of this patent is extended or adjusted under 35 U.S.C. 154(b) by 75 days.

(21) Appl. No.: 17/590,280

(22) Filed: Feb. 1, 2022

(65) Prior Publication Data
US 2022/0241094 A1    Aug. 4, 2022

Related U.S. Application Data

(60) Provisional application No. 63/144,261, filed on Feb. 1, 2021.

(51) Int. Cl.
*A61F 2/66*    (2006.01)
*A61F 2/50*    (2006.01)

(52) U.S. Cl.
CPC .... *A61F 2/6607* (2013.01); *A61F 2002/5018* (2013.01); *A61F 2002/5069* (2013.01)

(58) Field of Classification Search
CPC ............ A61F 2/6607; A61F 2002/5018; A61F 2002/5069
See application file for complete search history.

(56) References Cited

U.S. PATENT DOCUMENTS 3,671,978 A    6/1972    May
3,956,775 A *  5/1976    Moore ................... A61F 2/6607
                                                           623/50

(Continued)

FOREIGN PATENT DOCUMENTS

| CN | 1321621 C | 6/2007 |
| EP | 1788987 B1 | 7/2016 |
| WO | 00/42952 A1 | 7/2000 |

*Primary Examiner* — Matthew J Lawson
*Assistant Examiner* — Maximilian Tobias Spencer
(74) *Attorney, Agent, or Firm* — DINSMORE & SHOHL LLP

(57) ABSTRACT

A prosthetic foot includes a foot portion and a switching adapter. The switching adapter includes a first member coupled to the foot portion, a second member, a third member interposed between the first member and the second member, and a locking mechanism. The third member has a first side wall and a second side wall larger in length than the first side wall. The third member is configured to rotate relative to the first member and the second member towards a first position, thereby placing the prosthetic device in a walking mode. The third member is further configured to rotate relative to the first member and the second member towards a second position, thereby placing the prosthetic device in a running mode. The locking mechanism is configured to rotate with the third member in response to rotation of the third member.

16 Claims, 7 Drawing Sheets

(56) References Cited

U.S. PATENT DOCUMENTS

| | | |
|---|---|---|
| 4,795,474 A | 1/1989 | Horvath |
| 4,988,361 A | 1/1991 | Cooper |
| 5,135,529 A | 8/1992 | Paxon et al. |
| 5,358,526 A | 10/1994 | Tornier |
| 5,507,818 A | 4/1996 | McLaughlin |
| 6,402,790 B1 | 6/2002 | Celebi |
| 7,520,904 B2 | 4/2009 | Christensen |
| 7,578,852 B2 | 8/2009 | Townsend et al. |
| 9,326,862 B2 | 5/2016 | Smith et al. |
| 9,993,358 B2 | 6/2018 | Celebi et al. |
| 10,342,680 B2 | 7/2019 | Nijman et al. |
| 10,420,656 B2 | 9/2019 | Olafsson et al. |
| 10,792,171 B2 | 10/2020 | Ramirez |
| 2003/0181985 A1 | 9/2003 | Keller et al. |
| 2005/0038522 A1* | 2/2005 | Helenberger ............. A61F 2/76 623/36 |
| 2010/0161077 A1* | 6/2010 | Boone ....................... A61F 2/80 623/53 |
| 2015/0216667 A1 | 8/2015 | Monaghan |
| 2017/0156893 A1* | 6/2017 | Olafsson ................... A61F 2/64 |
| 2019/0125552 A1* | 5/2019 | Day ....................... A61F 2/6607 |
| 2020/0289293 A1 | 9/2020 | Hendriks et al. |

\* cited by examiner

PROSTHETIC FOOT WITH SWITCHABLE WALKING AND JOGGING MODES

CROSS-REFERENCE TO RELATED APPLICATION

The present application claims the benefit of Provisional Application No. 63/144,261 filed on Feb. 1, 2021, the entire contents of which is incorporated herein by reference.

GOVERNMENT SUPPORT

This invention was made with government support under contract number W81XWH19C0031 awarded by the USA Med Research ACQ Activity of the Department of Defense. The government has certain rights in the invention.

TECHNICAL FIELD

The present specification generally relates to apparatus and methods for prosthetics and, more specifically, apparatus and methods for prosthetics for switching between walking and jogging modes.

BACKGROUND

Conventional prostheses may be designed to focus on functioning for walking or for running. This may result in users using two sets of prostheses to switch between these modes. Accordingly, a need exists for improved prostheses that allow the user to use the same prosthesis for walking and running by having a mechanism to easily switch between walking and running modes.

SUMMARY

In one embodiment, a prosthetic device includes a foot portion and a switching adapter. The switching adapter includes a first member coupled to the foot portion, a second member connected, a third member interposed between the first member and the second member, and a locking mechanism. The third member has a first side wall and a second side wall larger in length than the first side wall. The third member is configured to rotate relative to the first member and the second member towards a first position, thereby placing the prosthetic device in a walking mode. The third member is further configured to rotate relative to the first member and the second member towards a second position, thereby placing the prosthetic device in a running mode. The locking mechanism is configured to rotate with the third member in response to rotation of the third member. The locking mechanism is configured to allow rotation of the third member relative to the first member and the second member when engaged and to prevent rotation of the third member relative to the first member and the second member when not actuated.

In another embodiment, an adapter for switching a prosthetic device between a walking mode and a running mode is provided. The adapter includes a first member, a second member, and a third member interposed between the first member and the second member. The third member includes a first side wall and a second side wall opposite the first side wall. The second side wall is larger in length than the first side wall. The third member further includes a first surface position between the first side wall and the second side wall and a second surface opposite the first surface and positioned between the first side wall and the second side wall. The third member is configured to rotate relative to the first member and the second member towards a first position, thereby placing the prosthetic device in the walking mode and rotate relative to the first member and the second member towards a second position, thereby placing the prosthetic device in the running mode.

In yet another embodiment, a method for adjusting a prosthetic device includes actuating a locking mechanism for a switching adapter. The switching adapter includes a first member coupled to a foot portion of the prosthetic device, a second member, and a third member interposed between the first member and the second member. The third member has a first side wall and a second side wall larger in length than the first side wall. The method further includes rotating the third member relative to the first member and the second member from a first position to a second position. The method further includes releasing the locking mechanism, thereby locking the switching adapter in the second position.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figures 1A, 1B:
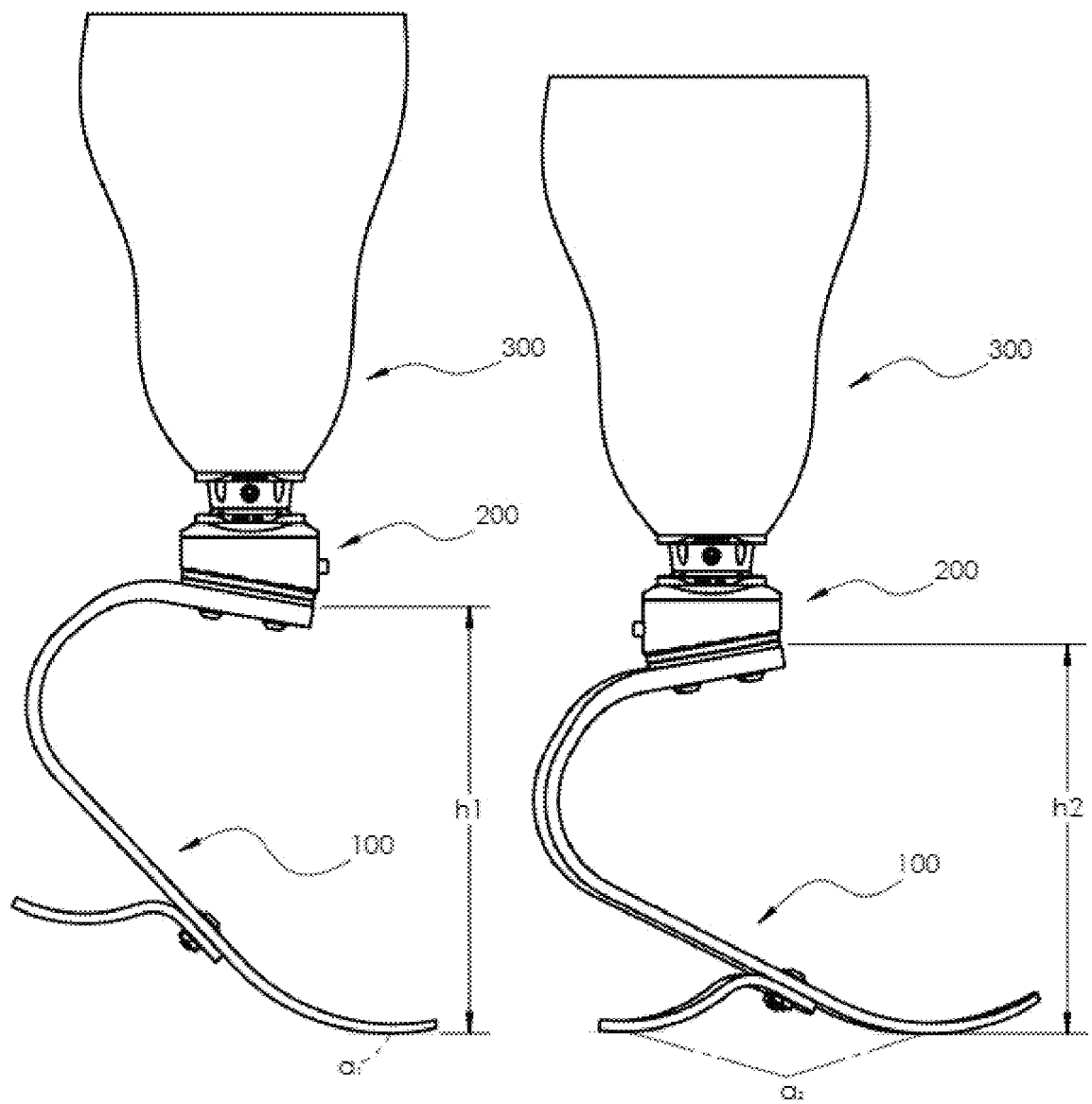
FIG. 1A schematically depicts a side view of a prosthetic device in a running mode, according to one or more embodiments shown and described herein.
FIG. 1B schematically depicts a side view of the prosthetic device in FIG. 1A in a walking mode, according to one or more embodiments shown and described herein.

Embodiments described herein are directed to a prosthetic device that is switchable between a running mode and a walking mode. Switching between the running mode and the walking mode adjusts a toe-in/toe-out alignment of the prosthetic device, a height alignment of the prosthetic device, and an anterior/posterior alignment of the prosthetic device. The prosthetic device includes a foot portion and a switching adapter. The switching adapter includes a first member coupled to the foot portion, a second member coupled to the pylon or pyramid adapter or prosthetic socket, a third member interposed between the first member and the second member, and a locking mechanism. The third member is configured to rotate relative to the first member and the second member.

Various embodiments of the method and apparatus and the operation of the method and apparatus are described in more detail herein. Whenever possible, the same reference numerals will be used throughout the drawings to refer to the same or like parts.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

As illustrated in FIGS. 1A and 1B, a prosthetic foot 100 is portrayed in a running mode and in a walking mode, respectively. The prosthetic foot 100 may differ in several aspects between the running mode and the walking mode. These aspects include: anterior/posterior alignment, toe-in/toe-out alignment, and height alignment. As a general rule of the anterior/posterior alignment, the walking mode may have prosthetic feet that are aligned with approximately ⅔ of the length of the foot in front of the pylon (pyramid adapter or socket) or weight line and ⅓ of the length of the foot behind the pylon (pyramid adapter or socket) or weight line while standing. The prosthetic feet in a running mode are aligned, relatively, with less of the overall foot in front and more of the overall foot behind the pylon (pyramid adapter or socket) or weight line. As compared to the walking mode, a heel of the prosthetic foot 100 is not in contact with the ground in a running mode. Accordingly, the alignment of the prosthetic foot 100 in the running mode results in a point contact almost directly underneath the mounting point of the prosthetic foot 100. The weight line refers to a vertical line passing through the center of gravity of a body of a user.

Regarding height alignment, the prosthetic foot 100 in the running mode may absorb higher loads and deflect more from the impact of running. To address the higher loads, the prosthetic foot 100 may be generally aligned to be approximately 1" taller than the prosthetic foot 100 in the walking mode. In other words, the prosthetic foot 100 may extend vertically taller (e.g., opposing the direction of gravity) in the running mode as compared to the walking mode for the same user. This difference in height is schematically illustrated when comparing FIGS. 1A and 1B, which illustrate the prosthetic foot 100 in the running mode and the walking mode respectively. FIG. 1A illustrates a mating surface between the prosthetic device 100 and a switching adapter 200, in the running mode, at a first height $h_1$ and FIG. 1B, illustrates the mating surface between the prosthetic device 100 and the switching adapter 200, in the walking mode, at a second height $h_2$. The heights $h_1, h_2$ may be defined as a distance between the mating surface of the prosthetic device 100 and the switching adapter 200 and the ground. As shown $h_1$ is larger in size as compared to $h_2$. Each height is measured from a ground contacting area of the foot.

Toe-in/toe-out alignment of the prosthetic foot 100 refers to a yaw of the prosthetic foot 100 (e.g., rotation of the foot around a vertical axis). This rotation is illustrated by an angle θ in FIG. 2B. The prosthetic foot 100 in the running mode typically is not turned outward relative to the body of the user. The prosthetic feet 100 in the walking mode are configured such that they are turned outward by approximately 3 to 8 degrees relative to the body of the user. In embodiments, prosthetic feet 100 may be configured such that they are turned outward by approximately 0 to 10 degrees relative to the body of the user.

Figures 2A, 2B:
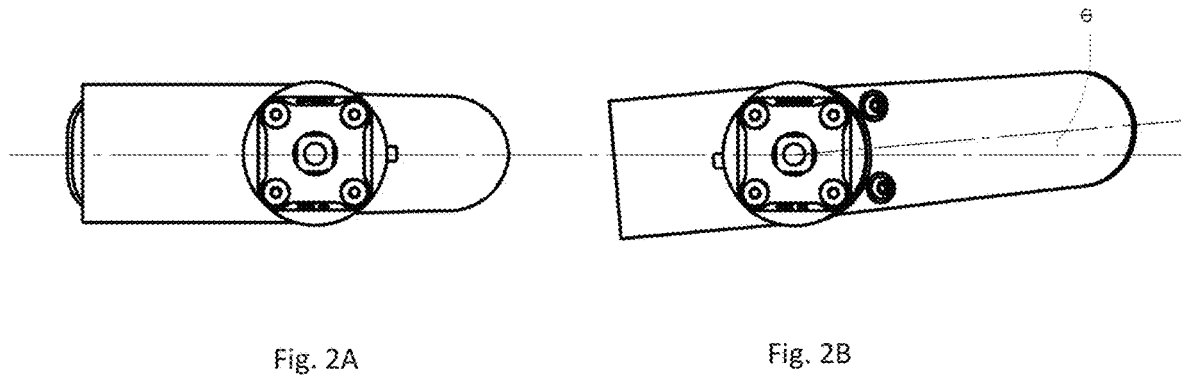
FIG. 2A schematically depicts a top view of the prosthetic device of FIG. 1A in the running mode, according to one or more embodiments shown and described herein.
FIG. 2B schematically depicts a top view of the prosthetic device of FIG. 1A in the walking mode, according to one or more embodiments shown and described herein.

FIG. 2A is a top view of the prosthetic foot in a running mode corresponding to FIG. 1A. FIG. 2B is a top view of the prosthetic foot in a walking mode corresponding to FIG. 1B. FIG. 1A illustrates that the prosthetic foot 100 defines a smaller contact area to the ground in comparison to the prosthetic foot 100 with that of FIG. 1B in a walking mode. The running mode defines a smaller contact area with the ground due to the heel of the prosthetic foot 100 being raised from the ground. Further, less of the toe portion of the prosthetic foot 100 may actually contact the ground when in the running mode. For example, and as illustrated in FIG. 1A, in the running mode the prosthetic foot 100 may have a contact area of $a_1$. As illustrated in FIG. 1B, in the walking mode the prosthetic foot 100 may have a contact area of $a_2$. In this example, the contact area $a_1$ is less than the contact area $a_2$.

Figure 3:
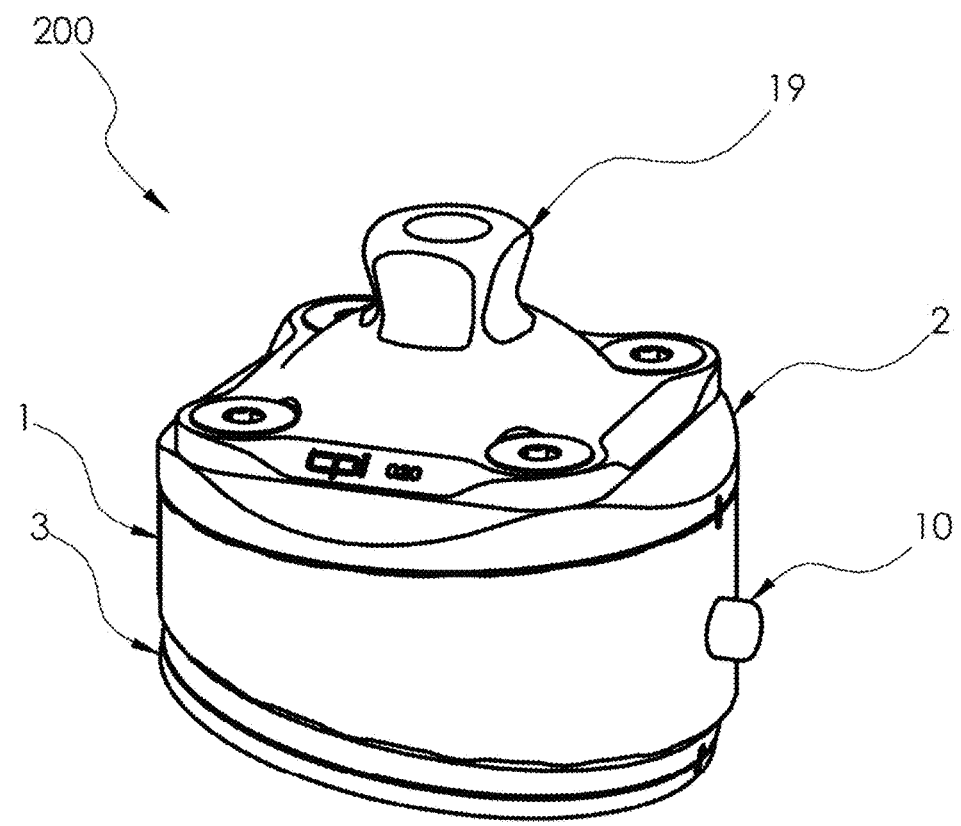
FIG. 3 schematically depicts a perspective view of a switching adapter for a prosthetic device, according to one or more embodiments shown and described herein.

Referring now to FIG. 3, a switching adapter 200 for the prosthetic foot 100 is illustrated, according to some embodiments. The switching adapter 200 may define a wedge-shaped profile held in place by sets of bearings connecting the prosthetic foot 100 to a bottom portion of the switching adapter 200. The switching adapter 200 may be further connected to a pylon, pyramid adapter or socket to a top portion of the switching adapter 200. The top portion is axially opposed to the bottom portion. In these embodiments, the height and the anterior/posterior alignment of the foot may be adjusted by rotating the wedge-shaped middle component 1 such that the prosthetic foot 100 is rotated about an axis perpendicular to the sagittal plane by a specific angle (for example, 20 degrees). This mechanism may also result in the toe in/toe out alignment change as part of the same switching motion, such that the foot rotates about the vertical axis. The switching mechanism will be described in further detail below, referring to the figures.

The switching adapter 200 is shown in varying embodiments in FIGS. 1-8. The switching adapter 200 defines a wedge-shaped profile and may include a wedge-shaped nutator or nutation wedge 1 (e.g., a third member), a nutation base 2 (e.g., a second member), a male pyramid mount 19 and a nutation adapter 3 (e.g., a first member). The wedge-shaped nutator or nutation wedge 1 may be interposed between the nutation base 2 and the nutation adapter 3. A first set of bearings may be positioned between the nutation adapter 3 and the nutation wedge 1. A second set of bearings may be positioned between the nutation base 2 and the nutation wedge 1. The first set of bearings and the second set of bearings may be equidistantly positioned away from a center axis of the nutation wedge 1. As discussed in greater detail herein, the center axis of the nutation wedge 1 may be aligned with the axis X-X' shown in FIG. 4. In embodiments, the first set of bearings and the second set of bearings are preloaded between the nutation base 2 and the nutation wedge 1.

The switching adapter 200 further includes a locking mechanism that is engaged by a button 10. The nutation wedge 1 is configured to rotate about a vertical axis X-X' relative to the male pyramid mount 19 and configured to rotate about the axis Y-Y' relative to the nutation adapter 3 in response to engaging the button 10. The nutation adapter 3 may couple the switching adapter 200 to the prosthetic foot 100. The male pyramid mount 19 may couple to a pylon or pyramid adapter or socket 300 (as illustrated in FIGS. 1A and 1B).

Figure 5:
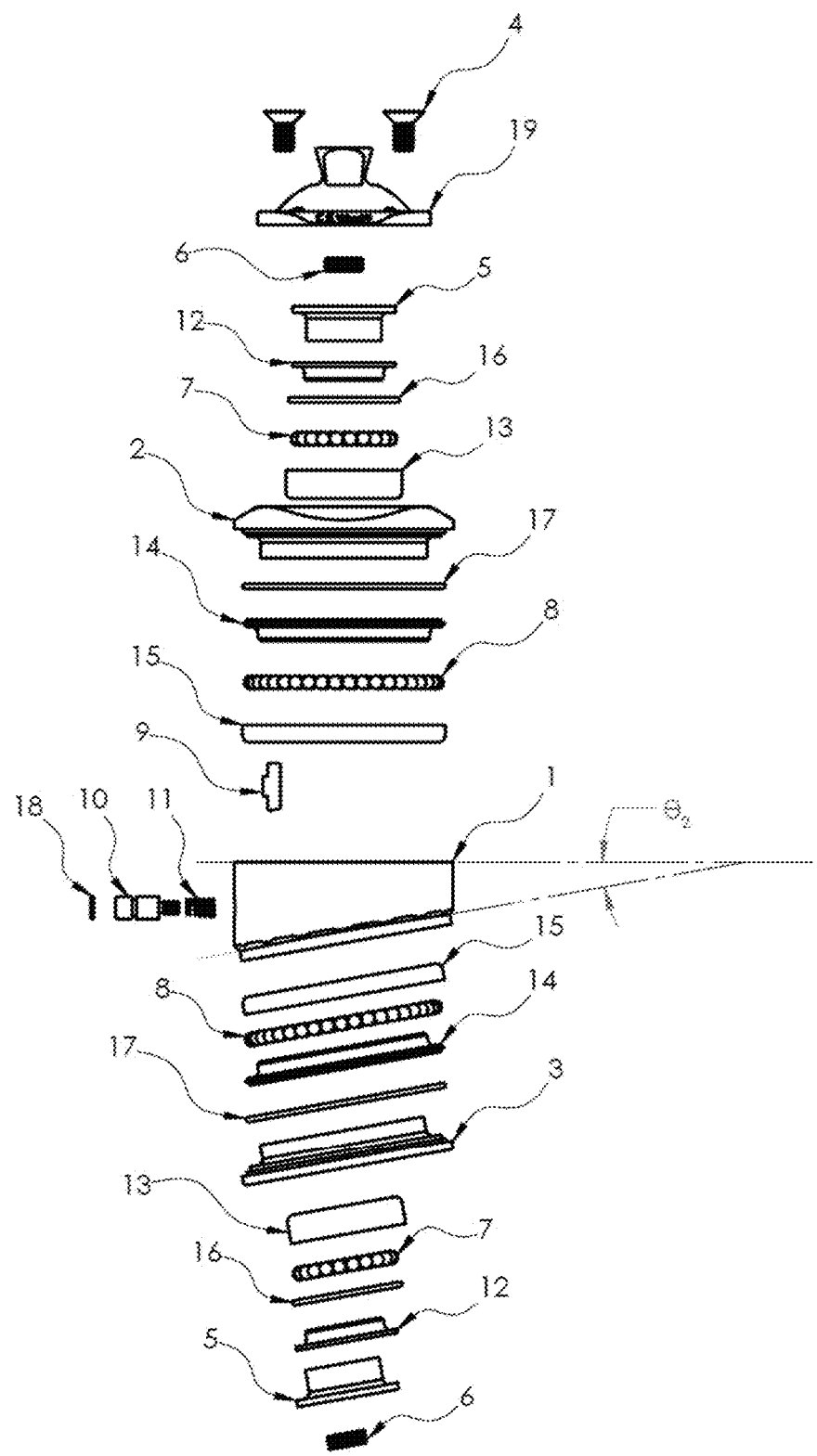
FIG. 5 schematically depicts a side, exploded view of the switching adapter of FIG. 3, according to one or more embodiments shown and described herein.
Figure 6:
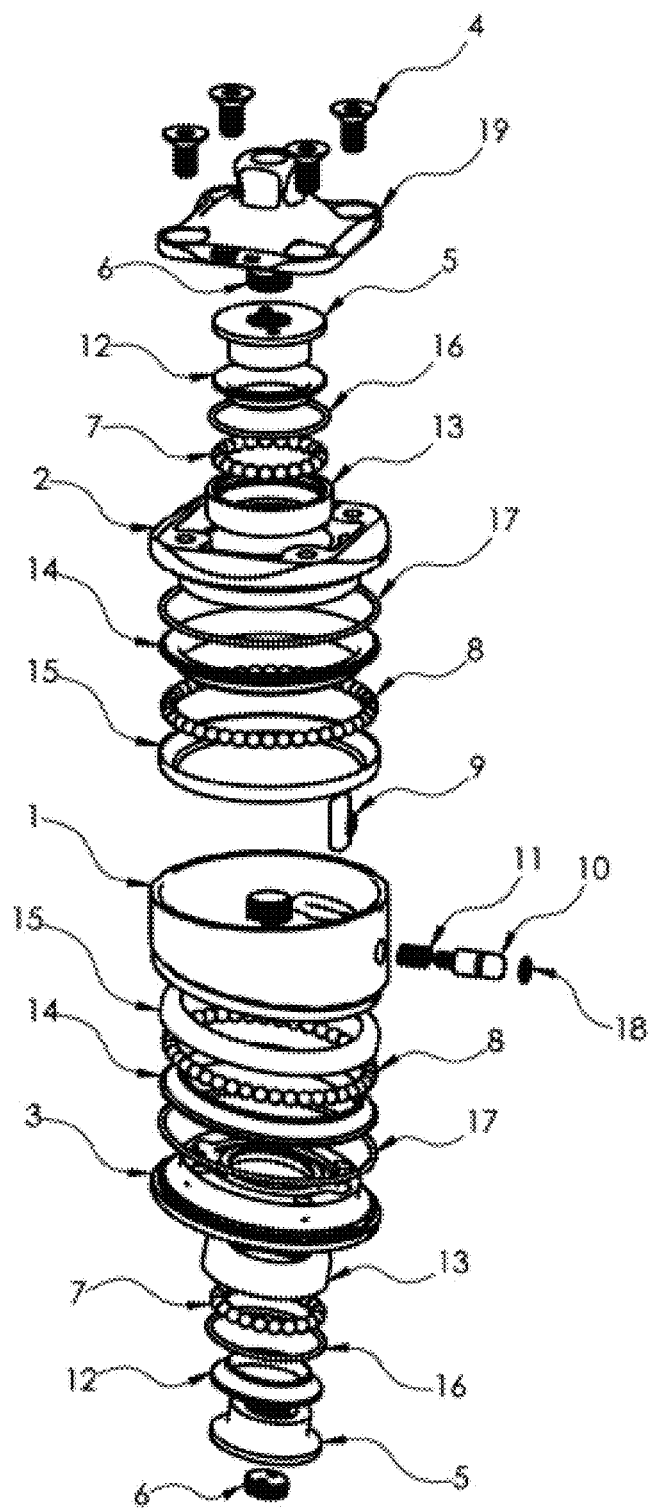
FIG. 6 schematically depicts a perspective, exploded view of the switching adapter of FIG. 3, according to one or more embodiments shown and described herein.

The nutation wedge 1 may be profiled to be obliquely truncated from a vertical column. The column may be a cylinder or any other suitable shape. The nutation wedge 1 may include a top surface, a bottom surface, a first side wall, and a second side wall. In embodiments, the components of the nutation wedge 1 (e.g., top surface, bottom surface, first side wall, second side wall) co-operate to define a cylindrical wedge shape for the nutation wedge 1. The top surface and the bottom surface may have an angularly offset $\theta_2$ relative to each other. This angular offset $\theta_2$ is illustrated in FIG. 5. In embodiments, the angular offset $\theta_2$ of the top surface relative to the bottom surface may be between 0 to 15 degrees. In embodiments, the angular offset $\theta_2$ of the top surface relative to the bottom surface may be between 15 to 30 degrees. In embodiments, the angular offset $\theta_2$ of the top surface relative to the bottom surface may be between 30 to 45 degrees. In embodiments, the angular offset $\theta_2$ of the top surface relative to the bottom surface may be between 45 to 60 degrees. In embodiments, either the top surface or bottom surface is perpendicular to the vertical axis. In embodiments, neither the top surface nor the bottom surface is perpendicular to the vertical axis.

Figure 4:
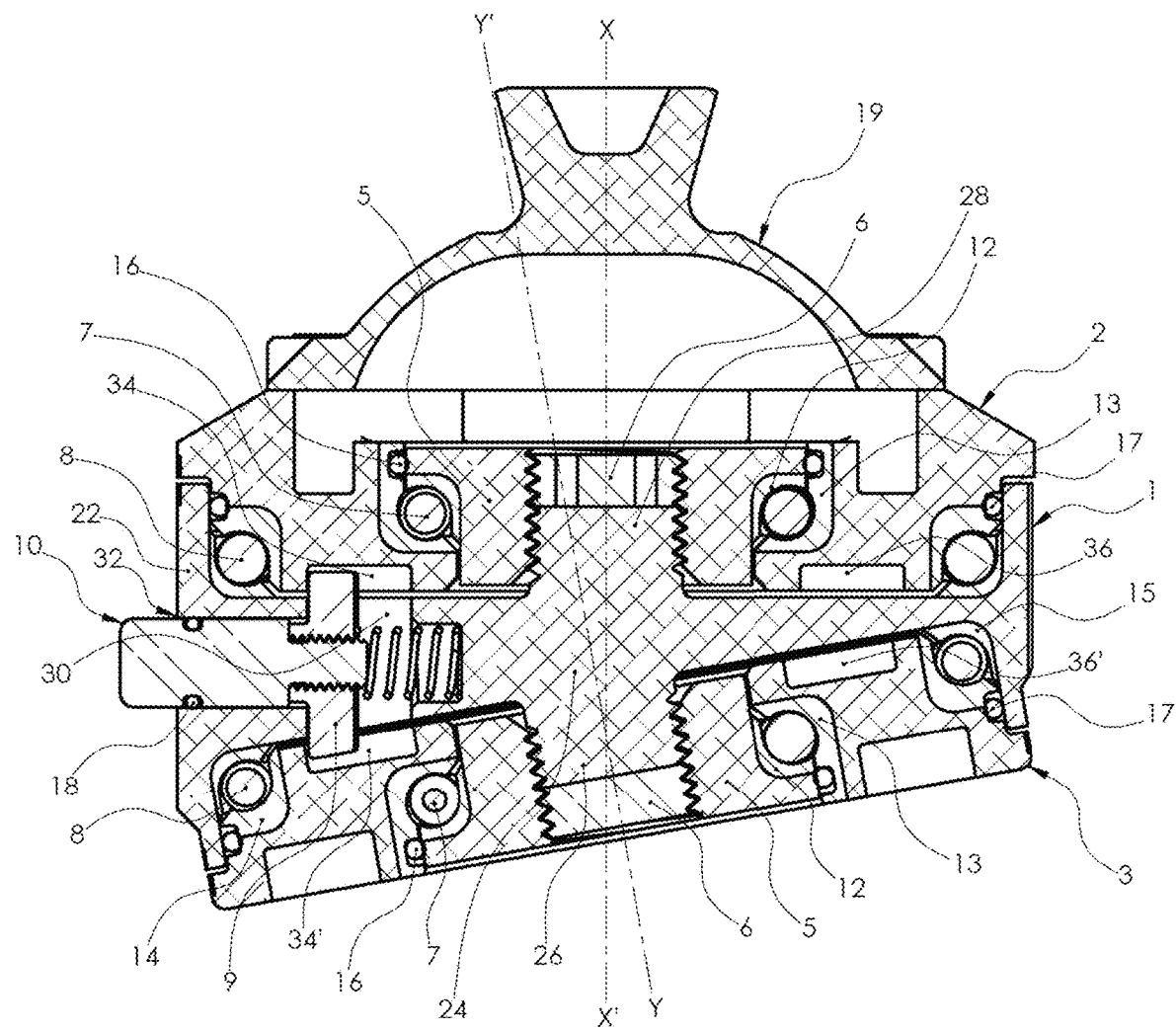
FIG. 4 schematically depicts a cross-sectional view of the switching adapter of FIG. 3, according to one or more embodiments shown and described herein.

Referring to a cross-sectional view of the switching adapter 200, as shown in FIG. 4, the nutation wedge 1 has a cylindrical wall 22. From the exploded elevation view in FIG. 5, it can be seen that the cylindrical wall 22 of the nutation wedge 1 is wedge-shaped. The height of the wall 22 on the first side wall of the cross section is largest and may gradually taper off towards the second side wall of cross section. Within the wall 22 and connected to the wall 22 is a beveled disk 24 (see FIG. 4) having a wedged cross section from one side of the wall to the opposite side. In the center of the disk 24 may be a stud 28 protruding from the top side of the disk 24. The stud 28 and the wall 22 may define a groove around the stud 28 on the top side of the disk 24.

In embodiments, the stud 28 may include a screw thread and may define a cylindrical profile. The axis of the stud 28 may coincide with the axis X-X' of the nutation wedge 1. At the bottom side of the disk 24, a stud 26 protrudes from the center of disk 24 and a groove is formed between the stud 26 and the wall 22. In embodiments, the stud 26 also has a screw thread and may define a cylindrical profile. The axis Y-Y' of the cylindrical stud 26 may be generally perpendicular to the bottom side of the disk 24 and may have an angular offset from the axis X-X'. This angular offset may be the same as the angular offset between the top surface and bottom surface of the nutation wedge 1.

In embodiments, both the top stud 28 and bottom stud 26 are angled with respect to the vertical axis X-X', such that the axis of the top stud 28 and the bottom stud 26 are offset with respect to each other. In other words, the normal axis of the top surface of the disk 24, (e.g., the direction perpendicular to the top surface of the disk 24) may be angled with respect to the normal axis of the bottom surface of the disk 24, such that the disk 24 is oblique or beveled. The outer wall 22 of the disk may have an oval-shaped or any other suitable shaped cross section in the plane perpendicular to the vertical axis X-X'.

The beveled disk 24 may be held in place by sets of bearings positioned on both sides of the beveled disk 24. The bearings may be held together with large studs and corresponding threaded components which fasten onto the studs after the bearing balls are inserted. In embodiments, the threads are fastened via jam screws. These components are screwed together and secured in order to create bearing preload, such that the mechanism has minimal backlash. In embodiments, a flathead (e.g., a hex drive flat head screw, left-handed hex drive flat head screw) or socket head screw may be used to lock the stud and joint cap 5 together by passing through a clearance hole in the joint cap and threading into a tapped hole in the stud.

For example, and referring to FIG. 4, a joint cap 5 may be threaded onto the top stud 28 and secured with a jam screw 6. The nutation base 2 is positioned to fit in the top groove around the joint cap 5 with the ball bearings 7 between the joint cap 5 and the nutation base 2. The edge of the nutation base 2 rests on the wall 22. The nutation base 2 has two opposing locking slots 34, 36, one on each side of the axis X-X'. The two opposing lock slots 34, 36 hold the components of the switching adapter 200 in place when the switching adapter 200 is in the running mode or the walking mode. The ball bearings 7 may be placed between the cap inner race 12 and the cap outer race 13. In embodiments, the cap inner race 12 and the cap outer race 13 may be separate components constructed of a suitably hard material to serve as a bearing race or may be machined directly into the supporting mechanical components. An O-ring 16 may be utilized to seal the space from ingress. The ball bearings 8 within the nutation wedge inner race 14 and the nutation wedge outer race 15 may be positioned between the nutation base 2 and the wall 22 with an O-ring 17 to seal the edges. The ball bearings may be replaced with roller bearings. A male pyramid mount 19 may be placed on the top of the nutation base 2 and secured with screws 4. The male pyramid mount 19 may be an off-the-shelf standard size product.

On the bottom side of disk 24, a joint cap 5 may also be threaded onto the bottom stud 26 and secured with a jam screw 6. A nutation adapter 3 may then be fit into the groove between the joint cap 5 and the wall 22. The edge of the nutation adapter 3 rests on the wall 22. The nutation adapter 3 has two opposing locking slots 34', 36', one on each side of the axis Y-Y'. Similar to the configuration on the top side of the disk 24, the ball bearings 7 are positioned between the joint cap 5 and the nutation adapter 3. The ball bearings 8 are positioned between the nutation adapter 3 and the wall 22. The ball bearings 7 may be placed between the cap inner race 12 and the cap outer race 13. In embodiments, the cap inner race 12 and the cap outer race 13 may be separate components constructed of a suitably hard material to serve as a bearing race or may be machined directly into the supporting mechanical components. The ball bearings 8 are within the nutation wedge inner race 14 and the nutation wedge outer race 15. The O-rings 16 and 17 are used to seal the edges.

The sets of bearings on either side of the wedge-shaped disk are aligned on an offset axis from each other, corresponding to the shape of the wedge. The bearing rings absorb load on a diagonal, to help the mechanism handle twisting/moment loads, while also facilitating rotation around the desired axes when the switching adapter is in an unlocked state.

On a first side of the cross section in FIG. 4, a hole 32 is situated in the wall 22 and connected to a cavity 30 within the disk 24. A locking member 9 may be lodged in place by a compression spring 11. A button 10 may be positioned in the cavity 30 through the hole 32 and may be pushed against the compression spring 11 to unlock the locking member 9.

When a user pushes on the button 10 to release the locking member 9, the nutation wedge 1 may be rotated about the axis X-X' along with both top and bottom joint caps 5 such that the axis Y-Y' is rotated about the axis X-X'.

In embodiments, the axis Y-Y' has an angular offset relative to the X-X' axis between 2 and 10 degrees. In embodiments, the axis Y-Y' has an angular offset between 0 and 15 degrees. In embodiments, the axis Y-Y' has an angular offset between 15 and 30 degrees. In embodiments, the axis Y-Y' has an angular offset between 30 and 45 degrees. In embodiments, the axis Y-Y' has an angular offset between 45 and 60 degrees. A center axis of the nutation base 2 and a center axis of the nutation adapter 3 may have a shared axis. In embodiments, the shared axis extends along the axis X-X'. A center axis of the nutation wedge 1 may have an angular offset relative to the shared axis. In embodiments, the center axis of the nutation wedge 1 extends along axis Y-Y'. In embodiments, the center axis of the nutation wedge 1 may remain constant throughout the rotation of the nutation wedge 1.

To switch between the walking and the running mode, the button 10 is engaged. This disengages the locking mechanism by pushing the locking member 9 out of a corresponding locking slot 34, 34'. The user then rotates the wedge-shaped disk 24, including the button 10, in the range of 170-180 degrees or 180-190 degrees with respect to the pyramid mount 19 and 180 degrees with respect to the nutation adapter 3, essentially the foot. In embodiments, the user may rotate the wedge-shaped disk 24, including the button 10, to exactly 180 degrees with respect to the pyramid mount 19 and 180 degrees with respect to the nutation adapter 3, essentially the foot. The user may then hold the prosthetic foot 100 during the rotation of the nutation wedge 1 to prevent the prosthetic foot 100 from rotating. When the button 10 is released, the locking member 9 drops into the other detent 36, 36' on the other side of the axis X-X' and Y-Y'. The button 10 may be placed either in the front of the adapter 200 or the rear of the adapter 200, or elsewhere. Other types of locking mechanism may be used for the design such as the locking mechanisms used in U.S. Pat. Nos. 4,795,474 or 10,420,656B2.

Referring back to FIGS. 1A, 1B and 4, as the switch is made between the walking and the running modes, the nutation wedge 1 is rotated such that the larger side of the wedge is rotated between the toe side of the foot and the heel side of the foot. If the pylon or socket stays in an upright position, the contact between the adapter 200 and the top portion of the prosthetic foot 100 is a slope going upward (e.g., opposing gravity) from the heel to the toe side of the foot during the walking mode, as shown in FIG. 1B. In contrast, in the running mode, the contact surface between the adapter 200 and the top portion of the prosthetic foot 100 is a slope going downward (e.g., towards gravity) from the heel to the toe side of the prosthetic foot 100, forcing the prosthetic foot 100 to rotate about an axis perpendicular to the sagittal plane and thereby increasing the height of the prosthetic foot 100 and decreasing the contact area of the prosthetic foot 100, as shown in FIG. 1A in comparison with FIG. 1B.

To switch between the walking mode and the running mode, the nutation wedge 1 of the adapter 200 may be rotated approximately 170 to 180 degrees or 180 to 190 degrees with respect to the nutation adapter 3 and with respect to the pyramid mount 19. In embodiments, the user may rotate the wedge-shaped disk 24, including the button 10, to exactly 180 degrees respect to the nutation adapter 3 and with respect to the pyramid mount 19. This facilitates for desired changes for toe-in and toe-out configurations in the walking mode and the running mode. The nutation wedge 1 may be rotated clockwise or counterclockwise. In an example, for a right foot, to switch from the walking mode to the running mode, the nutation wedge 1 is rotated clockwise 175 degrees or counterclockwise 185 degrees with respect to the pyramid mount 19, resulting in a toe-in alignment. In another example, to switch from the running mode to the walking mode, the nutation wedge 1 is rotated clockwise 185 degrees or counterclockwise 175 degrees with respect to the pyramid mount 19, resulting in a toe-out alignment. A mirror-image process applies for a left foot. In this example, to switch a left foot from the walking mode to the running mode, the nutation wedge 1 is rotated clockwise 185 degrees or counterclockwise 175 degrees with respect to the pyramid mount 19, resulting in a toe-in alignment. Following with this example, to switch from the running mode to the walking mode, the nutation wedge 1 is rotated clockwise 175 degrees or counterclockwise 185 degrees with respect to the pyramid mount 19, resulting in a toe-out alignment.

In embodiments, the yaw rotation may between about 3 to 8 degrees for the prosthetic foot 100 in the walking mode. However, varying angles are contemplated and envisioned based on the design of the prosthetic foot 100. In other words, the design may be configured to operate having an offset angle from 0 degrees to 10 degrees. The angle may also be set by the user's preferences. For example, at 0 degrees the user prefers not to have a yaw difference between the walking mode and the running mode. Alternatively, it is contemplated and possible to select multiple angular options for the offset angle. In embodiments, a more complex locking mechanism may be utilized to facilitate the user to choose their own preferred yaw angle.

In embodiments, a fastening method other than a screw thread stud may be used to hold the components of the switching adapter 200 together. For example, press fit components may be used and may not be cylindrical. In embodiments, off-the-shelf (OTS) bolts which screw into tapped holes may be used in the nutation wedge 1 instead of a stud. Multiple OTS bolts may be used on both sides of the nutation wedge.

Figure 7:
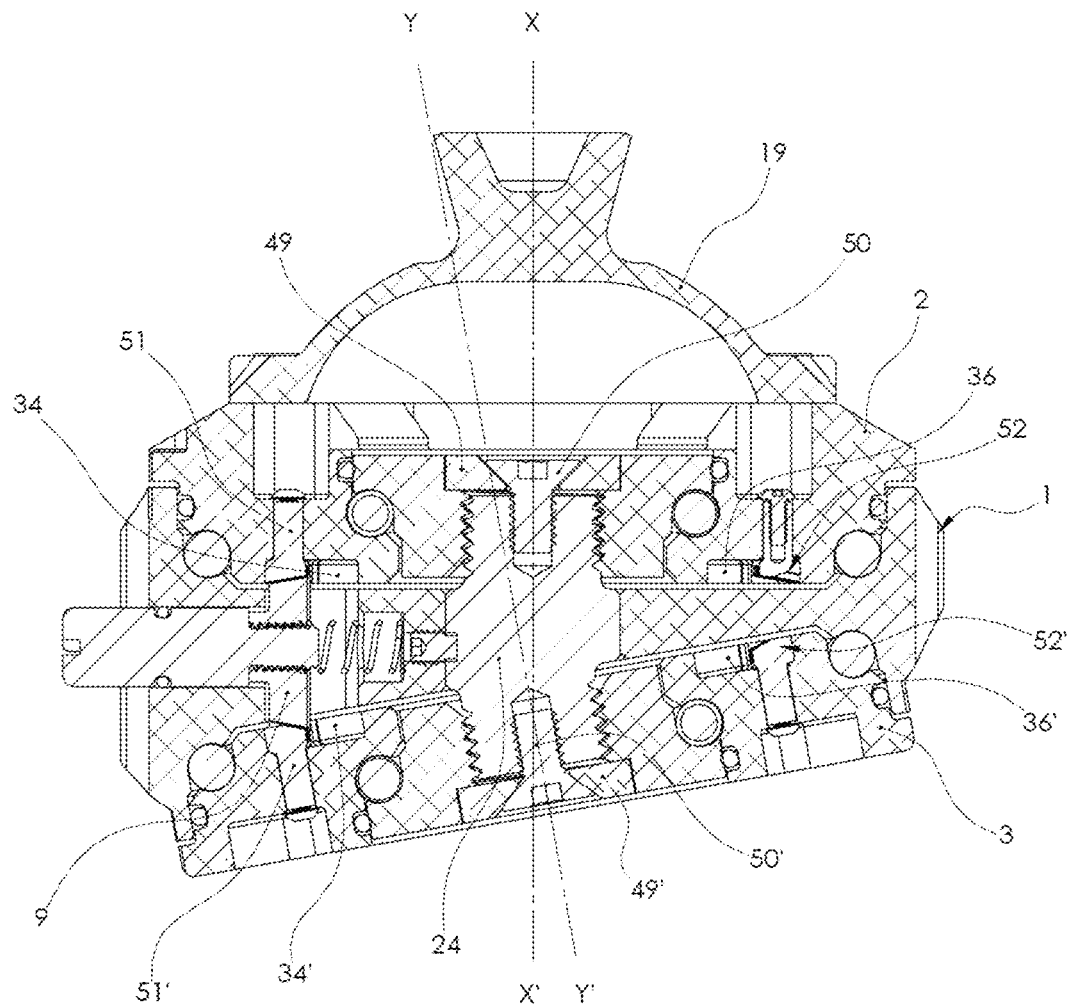
FIG. 7 schematically depicts a side, cross-sectional view of a switching adapter for the prosthetic device, according to one or more embodiments shown and described herein.

In embodiments, an alternative embodiment of a switching adapter 700 is illustrated in FIG. 7. In these embodiments, flat head fasteners 50, 50' (e.g., a flat head screw) are used to secure the stud and joint cap 5 together. Each of the flat head fasteners 50, 50' may extend through cap retaining plates 49, 49' prior to fastening the stud and joint cap 5 together. This embodiment facilitates for the use of a hexagonal fastener for securing the components of the switching adapter 700 in place. In embodiments, the flat head fasteners 50, 50' define a finer thread configuration relative to the threads of the stud. This may reduce an opportunity for the joint cap 5 to become less secured to the stud due to differences in thread pitch resulting in less axial translation between the joint cap 5 and the stud. In embodiments, the thread pitch between the stud and the joint cap 5 may be oppositely oriented. In this way, axial translation between the stud and the joint cap 5 may be reduced.

Figure 8:
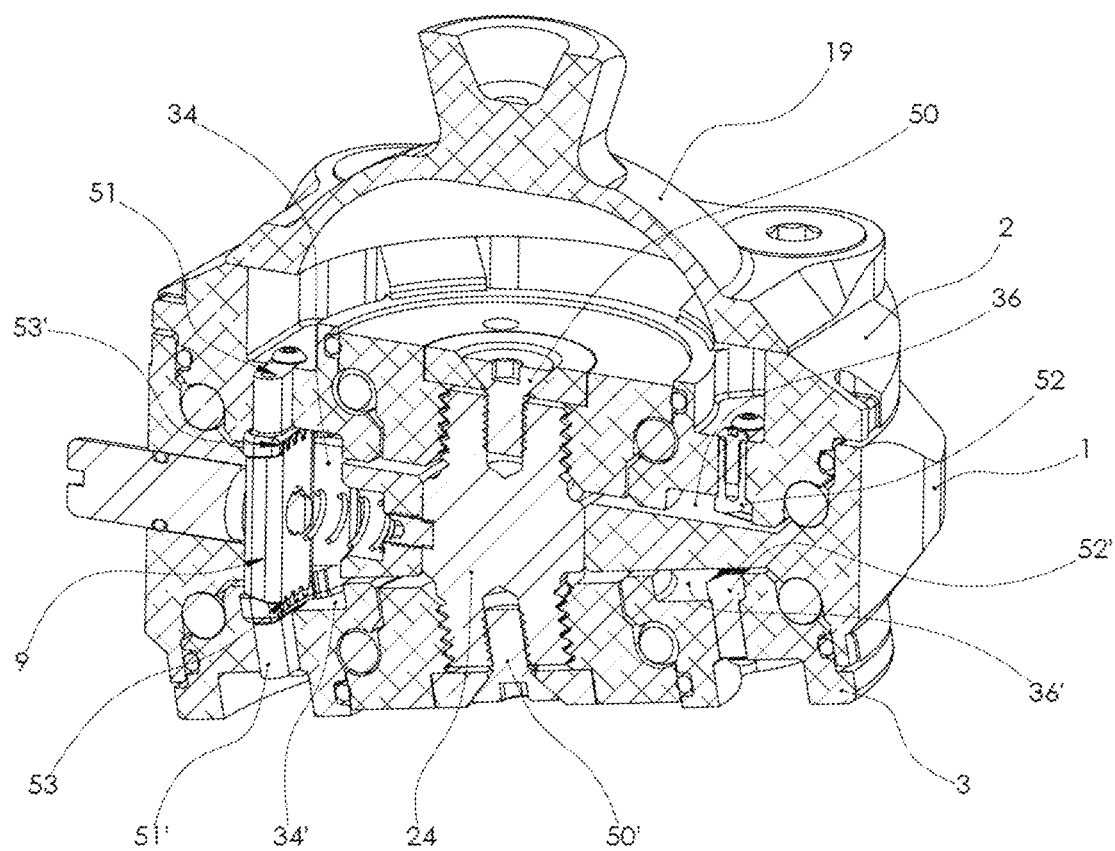
FIG. 8 schematically depicts a perspective, cross-sectional view of the switching adapter of FIG. 7, according to one or more embodiments shown and described herein.

FIG. 8 illustrates a locking mechanism for the nutation wedge 1 in the switching adapter 700, according to some embodiments. In these embodiments, the locking member 9 includes toothed interfaces 53, 53' on axial ends of the locking member 9. In these embodiments, the toothed interfaces 53, 53' interface with locking slots 51, 51' at the first position and locking slots 52, 52' at the second position. In these embodiments, the toothed interfaces 53, 53' may increase the surface friction of the locking member 9 within the two opposing lock slots 34, 36. This may reduce any axial movement (e.g., slack) within the switching adapter 700. In some embodiments, locking slots 51, 51' and locking slots 52, 52' define complimentary toothed interfaces to further enhance the surface friction of the locking member 9 within the two opposing lock slots 34, 36.

In embodiments, the third member is configured to rotate, relative to the first member and the second member, from the second position to the first position only in a first direction (e.g., either clockwise or counterclockwise) and to rotate from the first position to the second position only in a second direction (e.g., opposite the first direction). In embodiments, the third member is configured to rotate, relative to the first member and the second member, from the second position to the first position only in a first direction (e.g., either clockwise or counterclockwise) and to rotate from the first position to the second position in the same direction (e.g., continue rotating clockwise or counterclockwise).

From the above, it is to be appreciated that defined herein is a prosthetic device that is switchable between a running mode and a walking mode. Switching between the running mode and the walking mode adjusts a toe-in/toe-out alignment of the prosthetic device, a height alignment of the prosthetic device, and an anterior/posterior alignment of the prosthetic device. The prosthetic device includes a foot portion and a switching adapter. The switching adapter includes a first member coupled to the foot portion, a second member coupled to a pylon or pyramid adapter or socket, a third member interposed between the first member and the second member, and a locking mechanism. The third member is configured to rotate relative to the first member and the second member.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

What is claimed:

1. A prosthetic device comprising:
a foot portion having a heel side and a toe side; and
a switching adapter comprising:
a first member coupled to the foot portion;
a second member;
a third member interposed between the first member and the second member, the third member having a bottom surface adjacent the first member and a top surface adjacent the second member, the bottom and top surfaces being angled relative to each other;
the third member configured to rotate relative to the first member about a first center axis and relative to the second member about a second center axis, the first center axis having an angular offset relative to the second center axis;
the third member being rotatable relative to both the first and second member into a first position, thereby placing the prosthetic device in a walking mode and being rotatable relative to both the first member and the second member into towards a second position, thereby placing the prosthetic device in a running mode, an angle of the foot portion relative to the second member changing between the walking mode and the running mode such that the toe side is angled more downwardly relative to the heel side in the running mode than in the walking mode; and
a locking mechanism configured to allow rotation of the third member relative to the first member and the second member when engaged and to prevent rotation of the third member relative to the first member and the second member when not engaged.

2. The prosthetic device of claim 1, further comprising:
a first set of bearings disposed between the first member and the third member; and
a second set of bearings disposed between the second member and the third member.

3. The prosthetic device of claim 2, wherein the first set of bearings and the second set of bearings are equidistantly disposed away from a center axis of the third member.

4. The prosthetic device of claim 1, wherein the second member is coupled to at least one of a pyramid mount, a pylon or a prosthetic socket.

5. The prosthetic device of claim 1, wherein the angular offset of the first center axis relative to the second center axis remains a constant value during rotation of the first member.

6. The prosthetic device of claim 1, wherein the prosthetic device is configured to:
rotate the foot portion about a generally vertical axis to a first foot position in the walking mode; and
rotate the foot portion about the generally vertical axis to a second foot position in the running mode, the second foot position being angularly offset about the generally vertical axis to the first foot position.

7. The prosthetic device of claim 1, wherein:
the prosthetic device defines a first height of the foot portion from ground in the walking mode and a second height of the foot portion from ground in the running mode, the second height is larger in size relative to the first height; and
the prosthetic device is configured to rotate from a first angle relative to a body of a user of the prosthetic device in the walking mode to a second angle relative to the body of the user of the prosthetic device in the running mode.

8. The prosthetic device of claim 1, wherein the locking mechanism is configured to rotate with the third member in response to rotation of the third member.

9. A method for adjusting a prosthetic device, the method comprising:
providing a prosthetic device according to claim 1;
engaging the locking mechanism for the switching adapter;
rotating the third member relative to both the first member and the second member from the first position to the second position; and
releasing the locking mechanism, thereby locking the switching adapter in the second position.

10. The method of claim 9, wherein the prosthetic device is configured to:
rotate the foot portion about a generally vertical axis to a first foot position in the walking mode; and
rotate the foot portion about the generally vertical axis to a second foot position in the running mode, the second foot position being angularly offset about the generally vertical axis to the first foot position.

11. The method of claim 9, further comprising rotating the third member relative to the first member and the second member from the second position to the first position only in a first direction,
wherein rotating the third member relative to the first member and the second member from the first position to the second position is performed only in a second direction, the second direction being opposite in direction to the first direction.

12. An adapter for adjusting a prosthetic device between a walking mode and a running mode, the adapter comprising:
a first member;
a second member; and
a third member interposed between the first member and the second member, the third member having a bottom surface adjacent the first member and a top surface adjacent the second member, the bottom and top surfaces being angled relative to each other;
wherein the third member is configured to:
rotate relative to the first member about a first center axis and relative to the second member about a second center axis, the first center axis having an angular offset relative to the second center axis;
rotate relative to both the first member and the second member into a first position, thereby placing the prosthetic device in the walking mode; and
rotate relative to both the first member and the second member into a second position, thereby placing the prosthetic device in the running mode;
an angle of the first member relative to the second member changing between the walking mode and the running mode such that a toe side is angled more downwardly relative to a heel side in the running mode than in the walking mode.

13. The adapter of claim 12, further comprising:
a first set of bearings disposed between the first member and the third member; and
a second set of bearings disposed between the second member and the third member.

14. The adapter of claim 12, further comprising a disk disposed within the third member, the disk comprising:
a first threaded member centered on the first axis;
a first cap threadingly engaged to the first threaded member;
a second threaded member centered on the second axis; and
a second cap threadingly engaged to the second threaded member.

15. The adapter of claim 14, further comprising:
a third set of bearings disposed between the first member and the first cap; and
a fourth set of bearings disposed between the second member and the second cap.

16. The adapter of claim 12, further comprising a locking mechanism configured to allow rotation of the third member relative to the first member and the second member when engaged and to prevent rotation of the third member relative to the first member and the second member when not engaged, the locking mechanism comprising: a first toothed profile configured to engage a first complimentary profile defined into the first member when the locking mechanism is engaged; and a second toothed profile configured to engage a second complimentary profile defined into the second member when the locking mechanism is engaged.

* * * * *